United States Patent

Schwarz

Patent Number: 5,665,150
Date of Patent: Sep. 9, 1997

[54] DYE AND INK COMPOSITIONS

[75] Inventor: William M. Schwarz, Webster, N.Y.

[73] Assignee: Xerox Corporation, Stamford, Conn.

[21] Appl. No.: 720,061

[22] Filed: Sep. 27, 1996

[51] Int. Cl.$^6$ .................... C09D 11/02; C07D 307/91; C07D 307/92
[52] U.S. Cl. ................... 106/31.43; 106/31.27; 549/299
[58] Field of Search ............... 106/20 D, 22 R, 106/22 H; 549/299; 8/636

[56] References Cited

U.S. PATENT DOCUMENTS

| | | | |
|---|---|---|---|
| 4,115,404 | 9/1978 | Greenhalgh et al. | 548/433 |
| 4,122,087 | 10/1978 | Greenhalgh et al. | 548/433 |
| 5,183,888 | 2/1993 | Kenyon et al. | 549/299 |
| 5,189,181 | 2/1993 | Hall et al. | 549/299 |
| 5,215,313 | 6/1993 | Kenyon et al. | 549/299 |
| 5,413,613 | 5/1995 | Katsida et al. | 549/299 |
| 5,591,871 | 1/1997 | Suzuki et al. | 549/299 |

FOREIGN PATENT DOCUMENTS

| | | | |
|---|---|---|---|
| 551725 | 7/1993 | European Pat. Off. | 549/299 |
| 2103231 | 2/1983 | United Kingdom | 549/299 |

OTHER PUBLICATIONS

Greenhalgh et al, "The Synthesis of Quinodimethanes in the Benzodifuranone and Benzodipyrrolidone", Dyes and Pigments, vol. 1, pp. 103–120 (1980), No Month Available.

*Primary Examiner*—Helene Klemanski
*Attorney, Agent, or Firm*—Judith L. Byorick

[57] ABSTRACT

Disclosed is an ink jet printing process which comprises (1) incorporating into an ink jet printer an aqueous ink composition which comprises water, a humectant, and a colorant of the formula

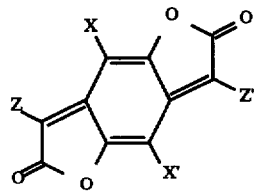

wherein X and X' each, independently of one another, are hydrogen, alkyl, halogen, ester, or amide, wherein Z and Z' each, independently of one another, are either (A):

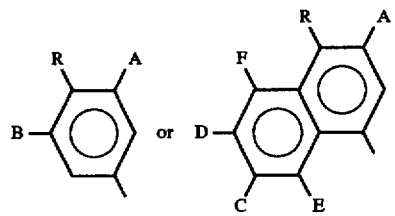

wherein R is hydrogen, hydroxy, alkoxy, aryloxy, ester, amine, amide, ether, thioether, or —$(O(CH_2)_y)_zOH$ wherein y is an integer of from 1 to 3 and z is an integer of from 1 to about 50, wherein A, B, C, D, E, and F each, independently of one another, are hydrogen, —COOH, —$SO_3M$, wherein M is a cation, or —NR"R'", wherein R" and R'" each, independently of one another, are hydrogen, alkyl, or aryl, wherein at least one of A, A', B, and B' is not hydrogen, or (B):

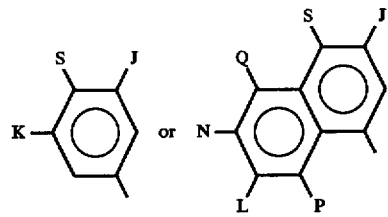

wherein S is hydrogen or —$(O(CH_2)_y)_zOH$, wherein y is an integer of from 1 to 3 and z is an integer of from 1 to about 50, wherein at least one S is not hydrogen; and wherein J, K, L, N, P, and Q each, independently of one another, are hydrogen, —COOH, —$SO_3M$, wherein M is a cation, or —NR"R'", wherein R" and R'" each, independently of one another, are hydrogen, alkyl, or aryl.

16 Claims, No Drawings

DYE AND INK COMPOSITIONS

The present invention is directed to dye compositions, to inks containing these dyes, and to printing processes employing these inks. More specifically, the present invention is directed to dyes soluble in aqueous media and suitable for use in aqueous inks, such as inks employed in thermal ink jet printing processes. One embodiment of the present invention is directed to an ink jet printing process which comprises (1) incorporating into an ink jet printer an aqueous ink composition which comprises water, a humectant, and a colorant of the formula

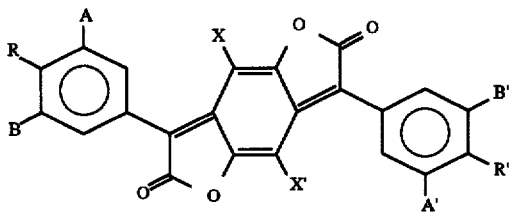

wherein (a) X and X' each, independently of one another, are hydrogen, alkyl, halogen, ester, or amide; (b) R and R' each, independently of one another, are hydrogen, hydroxy, alkoxy, aryloxy, ester, amine, amide, ether, thioether, or —(O(CH$_2$)$_y$)$_z$OH wherein y is an integer of from 1 to 3 and z is an integer of from 1 to about 50; (c) A, A', B, and B' each, independently of one another, are hydrogen, —COOH, —COOM, —SO$_3$H, —SO$_3$M, wherein M is a cation, or —NR"R'", wherein R" and R'" each, independently of one another, are hydrogen, alkyl, or aryl, wherein at least one of A, A', B, and B' is not hydrogen; or

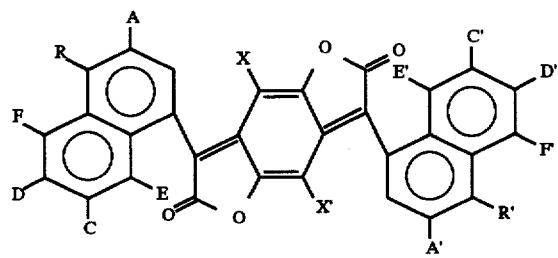

wherein (a) X and X' each, independently of one another, are hydrogen, alkyl, halogen, ester, or amide; (b) R and R' each, independently of one another, are hydrogen, hydroxy, alkoxy, aryloxy, ester, amine, amide, ether, thioether, or —(O(CH$_2$)$_y$)$_z$OH, wherein y is an integer of from 1 to 3 and z is an integer of from 1 to about 50; (c) A, A', C, C', D, D', E, E', F, and F' each, independently of one another, are hydrogen, —COOH, —COOM, —SO$_3$H, —SO$_3$M, wherein M is a cation, or —NR"R'", wherein R" and R'" each, independently of one another, are hydrogen, alkyl, or aryl, wherein at least one of A, A' C, C', D, D', E, E', F, and F' is not hydrogen; or

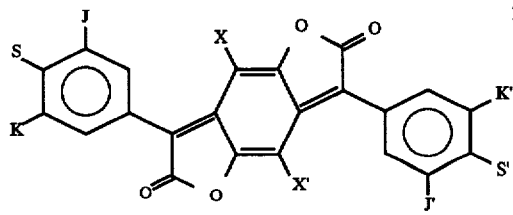

wherein (a) X and X' each, independently of one another, are hydrogen, alkyl, halogen, ester, or amide; (b) S and S' each, independently of one another, are hydrogen or —(O(CH$_2$)$_y$)$_z$OH, wherein y is an integer of from 1 to 3 and z is an integer of from 1 to about 50, wherein at least one of S and S' is not hydrogen; (c) J, J', K, and K' each, independently of one another, are hydrogen, —COOH, —COOM, —SO$_3$H, —SO$_3$M, wherein M is a cation, or —NR"R'", wherein R" and R'" each, independently of one another, are hydrogen, alkyl, or aryl; or

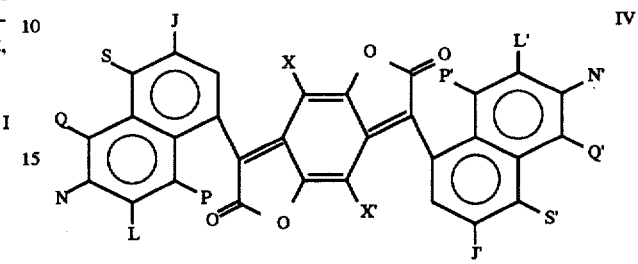

wherein (a) X and X' each, independently of one another, are hydrogen, alkyl, halogen, ester, or amide; (b) S and S' each, independently of one another, are hydrogen or —(O(CH$_2$)$_y$)$_z$OH, wherein y is an integer of from 1 to 3 and z is an integer of from 1 to about 50, wherein at least one of S and S' is not hydrogen; (c) J, J' L, L', N, N', P, P', Q, and Q' each, independently of one another, are hydrogen, —COOH, —COOM, —SO$_3$H, —SO$_3$M, wherein M is a cation, or —NR"R'", wherein R" and R'" each, independently of one another, are hydrogen, alkyl, or aryl; and (2) causing droplets of the ink composition to be ejected in an imagewise pattern onto a substrate. Another embodiment of the present invention is directed to dye compositions of the formula

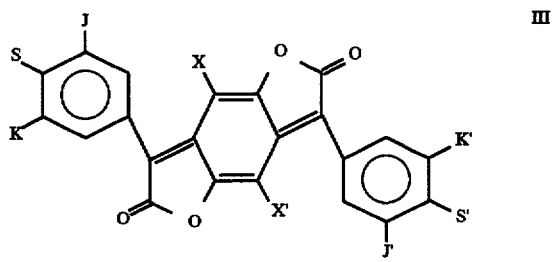

or

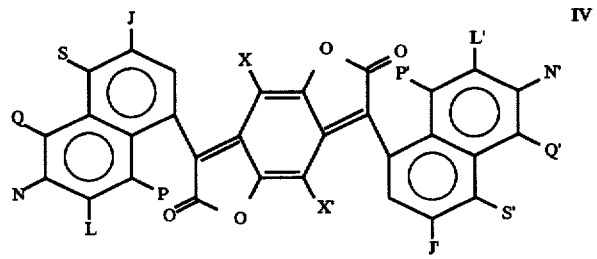

wherein (a) X and X' each, independently of one another, are hydrogen, alkyl, halogen, ester, or amide; (b) S and S' each, independently of one another, are hydrogen or —(O(CH$_2$)$_y$)$_z$OH, wherein y is an integer of from 1 to 3 and z is an integer of from 1 to about 50, wherein at least one of S and S' is not hydrogen; (c) J, J', K, K', L, L', N, N', P, P', Q, and Q' each, independently of one another, are hydrogen, —COOH, —COOM, —SO$_3$H, —SO$_3$M, wherein M is a cation, or —NR"R'", wherein R" and R'" each, independently of one another, are hydrogen, alkyl, or aryl.

Ink jet printing systems generally are of two types: continuous stream and drop-on-demand. In continuous stream ink jet systems, ink is emitted in a continuous stream under pressure through at least one orifice or nozzle. The stream is perturbed, causing it to break up into droplets at a fixed distance from the orifice. At the break-up point, the droplets are charged in accordance with digital data signals and passed through an electrostatic field which adjusts the trajectory of each droplet in order to direct it to a gutter for recirculation or a specific location on a recording medium. In drop-on-demand systems, a droplet is expelled from an orifice directly to a position on a recording medium in accordance with digital data signals. A droplet is not formed or expelled unless it is to be placed on the recording medium.

Since drop-on-demand systems require no ink recovery, charging, or deflection, the system is much simpler than the continuous stream type. There are two types of drop-on-demand ink jet systems. One type of drop-on-demand system has as its major components an ink filled channel or passageway having a nozzle on one end and a piezoelectric transducer near the other end to produce pressure pulses. The relatively large size of the transducer prevents close spacing of the nozzles, and physical limitations of the transducer result in low ink drop velocity. Low drop velocity seriously diminishes tolerances for drop velocity variation and directionality, thus impacting the system's ability to produce high quality copies. Drop-on-demand systems which use piezoelectric devices to expel the droplets also suffer the disadvantage of a slow printing speed.

The other type of drop-on-demand system is known as thermal ink jet, or bubble jet, and produces high velocity droplets and allows very close spacing of nozzles. The major components of this type of drop-on-demand system are an ink filled channel having a nozzle on one end and a heat generating resistor near the nozzle. Printing signals representing digital information originate an electric current pulse in a resistive layer within each ink passageway near the orifice or nozzle, causing the ink in the immediate vicinity to evaporate almost instantaneously and create a bubble. The ink at the orifice is forced out as a propelled droplet as the bubble expands. When the hydrodynamic motion of the ink stops, the process is ready to start all over again. With the introduction of a droplet ejection system based upon thermally generated bubbles, commonly referred to as the "bubble jet" system, the drop-on-demand ink jet printers provide simpler, lower cost devices than their continuous stream counterparts, and yet have substantially the same high speed printing capability.

The operating sequence of the bubble jet system begins with a current pulse through the resistive layer in the ink filled channel, the resistive layer being in close proximity to the orifice or nozzle for that channel. Heat is transferred from the resistor to the ink. The ink becomes superheated far above its normal boiling point, and for water based ink, finally reaches the critical temperature for bubble formation or nucleation of around 280° C. Once nucleated, the bubble or water vapor thermally isolates the ink from the heater and no further heat can be applied to the ink. This bubble expands until all the heat stored in the ink in excess of the normal boiling point diffuses away or is used to convert liquid to vapor, which removes heat due to heat of vaporization. The expansion of the bubble forces a droplet of ink out of the nozzle, and once the excess heat is removed, the bubble collapses on the resistor. At this point, the resistor is no longer being heated because the current pulse has passed and, concurrently with the bubble collapse, the droplet is propelled at a high rate of speed in a direction towards a recording medium. The resistive layer encounters a severe cavitational force by the collapse of the bubble, which tends to erode it. Subsequently, the ink channel refills by capillary action. This entire bubble formation and collapse sequence occurs in about 10 microseconds. The channel can be refired after 100 to 500 microseconds minimum dwell time to enable the channel to be refilled and to enable the dynamic refilling factors to become somewhat dampened. Thermal ink jet processes are well known and are described in, for example, U.S. Pat. Nos. 4,601,777, 4,251,824, 4,410,899, 4,412,224, and 4,532,530, the disclosures of each of which are totally incorporated herein by reference.

U.S. Pat. No. 4,122,087 (Greenhalgh et al.) and U.S. Pat. No. 4,115,404 (Greenhalgh et al.), the disclosures of each of which are totally incorporated herein by reference, discloses substituted 2,6-dioxo-2,6-dihydrobenzo[1:2-b, 4:5-b'] difurans or -dipyrroles and processes for their manufacture. The compounds are dyestuffs which are particularly useful in the form of aqueous dispersions for application to polyester textile materials.

C. W. Greenhalgh et al., "The Synthesis of Quinodimethanes in the Benzodifuranone and Benzodipyrrolidone Series," Dyes and Pigments, vol. 1, pp. 103–120 (1980), the disclosure of which is totally incorporated herein by reference, discloses the condensation of hydroquinone and 2,5-substituted hydroquinones with mandelic acids, or of 1,4-benzoquinone and 2,5-substituted 1,4-benzoquinones with mandelic acids or arylacetic acids, to yield 3,7-diaryl-2,6-dioxo-2,6-dihydrobenzo[1,2-b:4,5-b']difuran derivatives. Analogous benzodipyrrolidones are obtained from 1,4-phenylenediamine and N,N'-dimethyl-1,4-phenylenediamine. Both series are chromogens and have application as dyestuffs.

While known compositions and processes are useful for their intended purposes, a need remains for improved colorant compositions particularly suitable for use in ink jet printing inks. In addition, there is a need for ink jet inks with improved waterfastness. There is also a need for ink jet inks with improved lightfastness. Further, there is a need for ink jet inks in which lower concentrations of colorant are needed to obtain images of the desired color and intensity. Additionally, there is a need for ink jet inks which generate images of high color quality. There is also a need for ink jet inks with improved latency. A need also remains for ink jet inks containing dye colorants in which the dye exhibits little or no precipitation from the ink.

SUMMARY OF THE INVENTION

It is an object of the present invention to provide colorant compositions with the above noted advantages.

It is another object of the present invention to provide ink compositions with the above noted advantages.

It is yet another object of the present invention to provide improved colorant compositions particularly suitable for use in ink jet printing inks.

It is still another object of the present invention to provide ink jet inks with improved waterfastness.

Another object of the present invention is to provide ink jet inks with improved lightfastness.

Yet another object of the present invention is to provide ink jet inks in which lower concentrations of colorant are needed to obtain images of the desired color and intensity.

Still another object of the present invention is to provide ink jet inks which generate images of high color quality.

It is another object of the present invention to provide ink jet inks with improved latency.

It is yet another object of the present invention to provide ink jet inks containing dye colorants in which the dye exhibits little or no precipitation from the ink.

These and other objects of the present invention (or specific embodiments thereof) can be achieved by providing marking materials containing the specific colorant materials disclosed herein. One embodiment of the present invention is directed to an ink jet printing process which comprises (1) incorporating into an ink jet printer an aqueous ink composition which comprises water, a humectant, and a colorant of the formula

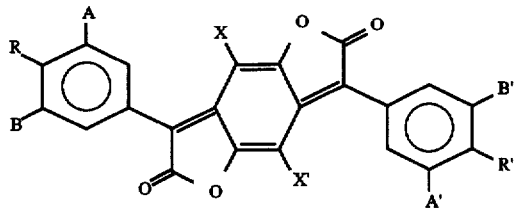

I wherein (a) X and X' each, independently of one another, are hydrogen, alkyl, halogen, ester, or amide; (b) R and R' each, independently of one another, are hydrogen, hydroxy, alkoxy, aryloxy, ester, amine, amide, ether, thioether, or —(O(CH$_2$)$_y$)$_z$OH wherein y is an integer of from 1 to 3 and z is an integer of from 1 to about 50; (c) A, A', B, and B' each, independently of one another, are hydrogen, —COOH, —COOM, —SO$_3$H, —SO$_3$M, wherein M is a cation, or —NR"R'", wherein R" and R'" each, independently of one another, are hydrogen, alkyl, or aryl, wherein at least one of A, A', B, and B' is not hydrogen; or

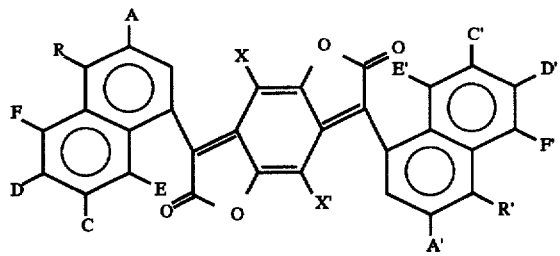

II wherein (a) X and X' each, independently of one another, are hydrogen, alkyl, halogen, ester, or amide; (b) R and R' each, independently of one another, are hydrogen, hydroxy, alkoxy, aryloxy, ester, amine, amide, ether, thioether, or —(O(CH$_2$)$_y$)$_z$OH, wherein y is an integer of from 1 to 3 and z is an integer of from 1 to about 50; (c) A, A', C, C', D, D', E, E', F, and F' each, independently of one another, are hydrogen, —COOH, —COOM, —SO$_3$H, —SO$_3$M, wherein M is a cation, or —NR"R'", wherein R" and R'" each, independently of one another, are hydrogen, alkyl, or awl, wherein at least one of A, A' C, C', D, D', E, E', F, and F' is not hydrogen; or

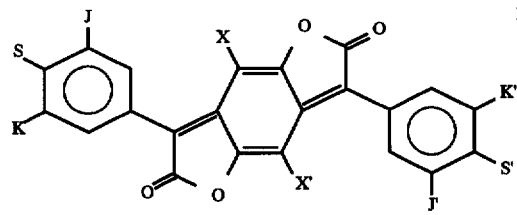

III wherein (a) X and X' each, independently of one another, are hydrogen, alkyl, halogen, ester, or amide; (b) S and S' each, independently of one another, are hydrogen or —(O(CH$_2$)$_y$)$_z$OH, wherein y is an integer of from 1 to 3 and z is an integer of from 1 to about 50, wherein at least one of S and S' is not hydrogen; (c) J, J', K, and K' each, independently of one another, are hydrogen, —COOH, —COOM, —SO$_3$H, —SO$_3$M, wherein M is a cation, or —NR"R'", wherein R" and R'" each, independently of one another, are hydrogen, alkyl, or aryl; or

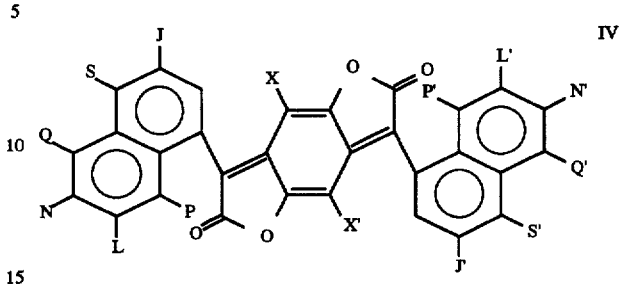

IV wherein (a) X and X' each, independently of one another, are hydrogen, alkyl, halogen, ester, or amide; (b) S and S' each, independently of one another, are hydrogen or —(O(CH$_2$)$_y$)$_z$OH, wherein y is an integer of from 1 to 3 and z is an integer of from 1 to about 50, wherein at least one of S and S' is not hydrogen; (c) J, J' L, L', N, N ', P, P', Q, and Q' each, independently of one another, are hydrogen, —COOH, —COOM, —SO$_3$H, —SO$_3$M, wherein M is a cation, or —NR"R'", wherein R" and R'" each, independently of one another, are hydrogen, alkyl, or aryl; and (2) causing droplets of the ink composition to be ejected in an imagewise pattern onto a substrate. Another embodiment of the present invention is directed to dye compositions of the formula

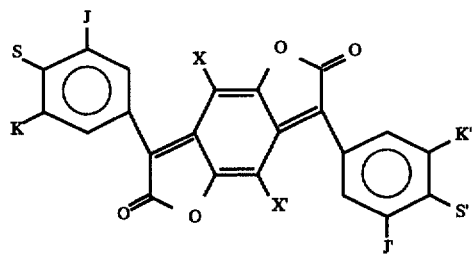

III or

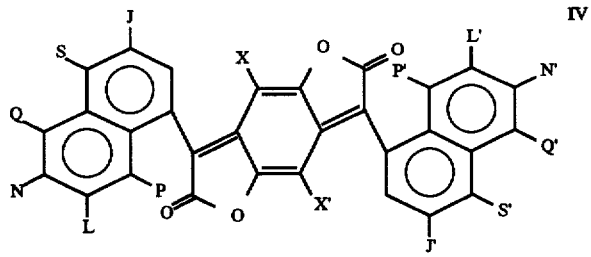

IV wherein (a) X and X' each, independently of one another, are hydrogen, alkyl, halogen, ester, or amide; (b) S and S' each, independently of one another, are hydrogen or —(O(CH$_2$)$_y$)$_z$OH, wherein y is an integer of from 1 to 3 and z is an integer of from 1 to about 50, wherein at least one of S and S' is not hydrogen; (c) J, J', K, K', L, L', N, N', P, P', Q, and Q' each, independently of one another, are hydrogen, —COOH, —COOM, —SO$_3$H, —SO$_3$M, wherein M is a cation, or —NR"R'", wherein R" and R'" each, independently of one another, are hydrogen, alkyl, or aryl.

DETAILED DESCRIPTION OF THE INVENTION

The dye compositions of the present invention can be of the general formula

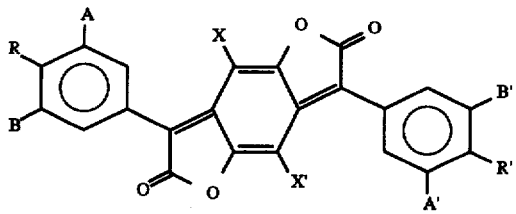

In compounds of Formula I, X and X', which may be either the same as each other or different from each other, are relatively electron withdrawing groups, and typically are hydrogen atoms; alkyl groups, typically with from 1 to about 5 carbon atoms, such as methyl, ethyl, propyl, or the like; halogen atoms, such as fluorine, chlorine, bromine, iodine, or the like; ester groups, typically of the general formula —C(O)OR, wherein R is an alkyl group, typically with from 1 to about 5 carbon atoms, such as methyl, ethyl, propyl, or the like, or an aryl group, typically with from about 6 to about 12 carbon atoms; or amide groups, typically of the general formula —CONRR", wherein R and R' each, independently of the other, are alkyl groups, typically with from 1 to about 5 carbon atoms, such as methyl, ethyl, propyl, or the like, or aryl groups, typically with from 6 to about 12 carbon atoms.

In compounds of Formula I, R and R', which may be either the same as each other or different from each other, are relatively high electron density groups, and typically are hydrogen atoms; hydroxy groups; alkoxy groups, wherein the alkyl portion typically has from 1 to about 5 carbon atoms, such as methoxy, ethoxy, propoxy, or the like; aryl oxy groups, typically with from about 6 to about 12 carbon atoms; ester groups, typically of the general formula —C(O)OR, wherein R is an alkyl group, typically with from 1 to about 5 carbon atoms, such as methyl, ethyl, propyl, or the like, or an aryl group, typically with from about 6 to about 12 carbon atoms; amine groups, typically of the general formula —NRR'R", wherein R, R', and R" each, independently of one another, are hydrogen atoms, alkyl groups, typically with from 1 to about 5 carbon atoms, such as methyl, ethyl, propyl, or the like, or aryl groups, typically with from about 6 to about 12 carbon atoms; amide groups, typically of the general formula —C(O)NRR', wherein R and R' each, independently of one another, are hydrogen atoms, alkyl groups, typically with from 1 to about 5 carbon atoms, such as methyl, ethyl, propyl, or the like, or aryl groups, typically with from 6 to about 12 carbon atoms; ether groups, typically of the general formula —OR, wherein R is an alkyl group, typically with from 1 to about 5 carbon atoms, such as methyl, ethyl, propyl, or the like, or an aryl group, typically with from about 6 to about 12 carbon atoms; thioether groups, typically of the general formula —SR, wherein R is an alkyl group, typically with from 1 to about 5 carbon atoms, such as methyl, ethyl, propyl, or the like, or an aryl group, typically with from about 6 to about 12 carbon atoms; or polyalkoxy groups, typically of the general formula —(O(CH$_2$)$_y$)$_z$OH, wherein y is an integer of from 1 to about 3 and z is an integer of from 1 to about 50, and preferably from 1 to about 20.

In compounds of Formula I, A, A', B, and B' are either hydrogen atoms or are relatively polar groups, such as —COOH; —COOM, wherein M is a cation, such as Li$^+$, Na$^+$, N$_4^+$, K$^+$, or the like; —SO$_3$H; —SO$_3$M, wherein M is a cation, such as Li$^+$, Na$^+$, NH$_4^+$, K$^+$, or the like; or amine groups, typically of the general formula —NR"R'", wherein R" and R'" each, independently of one another, are hydrogen, alkyl, or aryl. At least one of A, A', B, and B' is not hydrogen, and it is preferred that at least two of A, A', B, and B' be relatively polar groups.

The dye compositions of the present invention can also be of the general formula

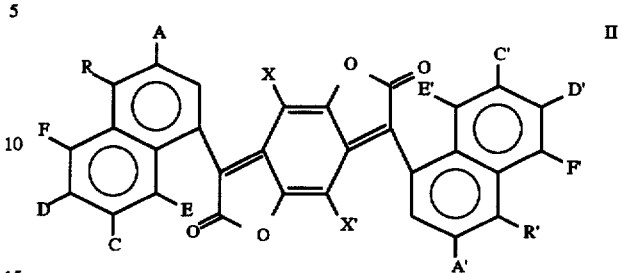

In compounds of Formula II, X and X', which may be either the same as each other or different from each other, are relatively electron withdrawing groups, and typically are hydrogen atoms; alkyl groups, typically with from 1 to about 5 carbon atoms, such as methyl, ethyl, propyl, or the like; halogen atoms, such as fluorine, chlorine, bromine, iodine, or the like; ester groups, typically of the general formula —C(O)OR, wherein R is an alkyl group, typically with from 1 to about 5 carbon atoms, such as methyl, ethyl, propyl, or the like, or an aryl group, typically with from 6 to about 12 carbon atoms; or amide groups, typically of the general formula —CONRR", wherein R and R' each, independently of the other, are alkyl groups, typically with from 1 to about 5 carbon atoms, such as methyl, ethyl, propyl, or the like, or aryl groups, typically with from 6 to about 12 carbon atoms.

In compounds of Formula II, R and R', which may be either the same as each other or different from each other, are relatively high electron density groups, and typically are hydrogen atoms; hydroxy groups; alkoxy groups, wherein the alkyl portion typically has from 1 to about 5 carbon atoms, such as methoxy, ethoxy, propoxy, or the like; aryloxy groups, typically with from about 6 to about 12 carbon atoms; ester groups, typically of the general formula —C(O)OR, wherein R is an alkyl group, typically with from 1 to about 5 carbon atoms, such as methyl, ethyl, propyl, or the like, or an aryl group, typically with from about 6 to about 12 carbon atoms; amine groups, typically of the general formula —NRR'R", wherein R, R', and R" each, independently of one another, are hydrogen atoms, alkyl groups, typically with from 1 to about 5 carbon atoms, such as methyl, ethyl, propyl, or the like, or aryl groups, typically with from about 6 to about 12 carbon atoms; amide groups, typically of the general formula —C(O)NRR', wherein R and R' each, independently of one another, are hydrogen atoms, alkyl groups, typically with from 1 to about 5 carbon atoms, such as methyl, ethyl, propyl, or the like, or aryl groups, typically with from about 6 to about 12 carbon atoms; ether groups, typically of the general formula —OR, wherein R is an alkyl group, typically with from 1 to about 5 carbon atoms, such as methyl, ethyl, propyl, or the like, or an aryl group, typically with from about 6 to about 12 carbon atoms; thioether groups, typically of the general formula —SR, wherein R is an alkyl group, typically with from 1 to about 5 carbon atoms, such as methyl, ethyl, propyl, or the like, or an aryl group, typically with from 6 to about 12 carbon atoms; or polyalkoxy groups, typically of the general formula —(O(CH$_2$)$_y$)$_z$OH, wherein y is an integer of from 1 to 3 and z is an integer of from 1 to about 50, and preferably from 1 to about 20.

In compounds of Formula II, A, A', C, C', D, D', E, E', F, and F' are either hydrogen atoms or are relatively polar groups, such as —COOH; —COOM, wherein M is a cation, such as Li⁺, Na⁺, NH₄⁺, K⁺, or the like; —SO₃H; —SO₃M, wherein M is a cation, such as Li⁺, Na⁺, NH₄⁺, K⁺, or the like; or amine groups, typically of the general formula —NR"R'", wherein R" and R'" each, independently of one another, are hydrogen, alkyl, or aryl. At least one of A, A', C, C', D, D', E, E', F, and F' is not hydrogen, and it is preferred that at least two of A, A', C, C', D, D', E, E', F, and F' be relatively polar groups.

The dye compositions of the present invention can also be of the general formula

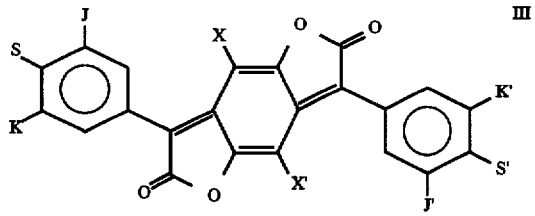

In compounds of Formula III, X and X', which may be either the same as each other or different from each other, are relatively electron withdrawing groups, and typically are hydrogen atoms; alkyl groups, typically with from 1 to about 5 carbon atoms, such as methyl, ethyl, propyl, or the like; halogen atoms, such as fluorine, chlorine, bromine, iodine, or the like; ester groups, typically of the general formula —C(O)OR, wherein R is an alkyl group, typically with from 1 to about 5 carbon atoms, such as methyl, ethyl, propyl, or the like, or an aryl group, typically with from about 6 to about 12 carbon atoms; or amide groups, typically of the general formula —CONRR", wherein R and R' each, independently of the other, are alkyl groups, typically with from 1 to about 5 carbon atoms, such as methyl, ethyl, propyl, or the like, or aryl groups, typically with from 6 to about 12 carbon atoms.

In compounds of Formula III, S and S', which may be either the same as each other or different from each other, are hydrogen atoms or polyalkoxy groups of the general formula —(O(CH₂)ᵧ)_zOH, wherein y is an integer of from 1 to 3 and z is an integer of from 1 to about 50, and preferably from 1 to about 20. At least one of S and S' is not hydrogen; that is, at least one of S and S' is a polyalkoxy group.

In compounds of Formula III, J, J', K, and K' are either hydrogen atoms or are relatively polar groups, such as, —COOH; —COOM, wherein M is a cation, such as Li⁺, Na⁺, NH₄⁺, K⁺, or the like; —SO₃H; —SO₃M, wherein M is a cation, such as Li⁺, Na⁺, NH₄⁺, K⁺, or the like; or amine groups, typically of the general formula —NR"R'", wherein R" and R'" each, independently of one another, are hydrogen, alkyl, or aryl.

The dye compositions of the present invention can also be of the general formula

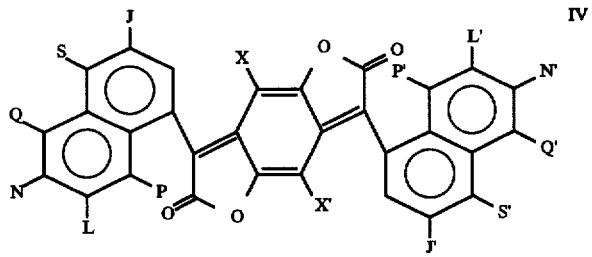

In compounds of Formula IV, X and X', which may be either the same as each other or different from each other, are relatively electron withdrawing groups, and typically are hydrogen atoms; alkyl groups, typically with from 1 to about 5 carbon atoms, such as methyl, ethyl, propyl, or the like; halogen atoms, such as fluorine, chlorine, bromine, iodine, or the like; ester groups, typically of the general formula —C(O)OR, wherein R is an alkyl group, typically with from 1 to about 5 carbon atoms, such as methyl, ethyl, propyl, or the like, or an aryl group, typically with from about 6 to about 12 carbon atoms; or amide groups, typically of the general formula —CONRR", wherein R and R' each, independently of the other, are alkyl groups, typically with from 1 to about 5 carbon atoms, such as methyl, ethyl, propyl, or the like, or aryl groups, typically with from 6 to about 12 carbon atoms.

In compounds of Formula IV, S and S', which may be either the same as each other or different from each other, are hydrogen atoms or polyalkoxy groups, typically of the general formula —(O(CH₂)ᵧ)_zOH, wherein y is an integer of from 1 to 3 and z is an integer of from 1 to about 50, and preferably from 1 to about 20. At least one of S and S' is not hydrogen; that is, at least one of S and S' is a polyalkoxy group.

In compounds of Formula IV, J, J', L, L', N, N', P, P', Q, and Q' are either hydrogen atoms or are relatively polar groups, such as —COOH; —COOM, wherein M is a cation, such as Li⁺, Na⁺, N₄⁺, K⁺, or the like; —SO₃H; —SO₃M, wherein M is a cation, such as Li⁺, Na⁺, NH₄⁺, K⁺, or the like; or amine groups, typically of the general formula —NR"R'", wherein R" and R'" each, independently of one another, are hydrogen, alkyl, or aryl.

The colorant compositions can be prepared by any desired or suitable process. For example, the basic chromophore can be prepared as disclosed in, for example, U.S. Pat. Nos. 4,115,404 and 4,122,087, the disclosures of each of which are totally incorporated herein by reference. The polar groups can be placed on the chromophores by any desired or suitable process, including those disclosed in, for example, U.S. Pat. Nos. 4,115,404 and 4,122,087. Alternatively, staffing materials which contain the desired substituents in the desired positions can be employed in the synthesis of the chromophore. Illustrative examples include the following:

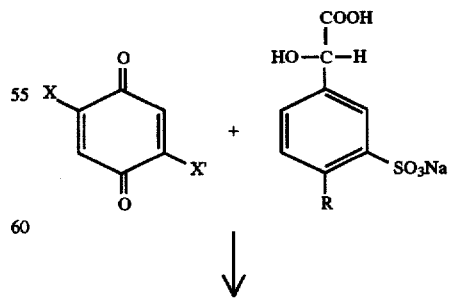

-continued

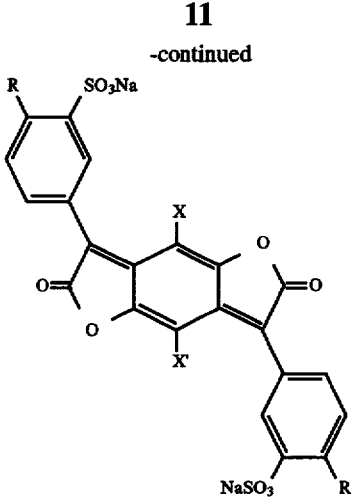

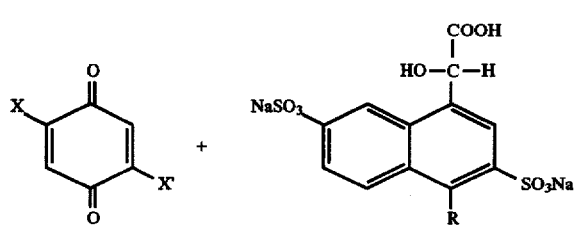

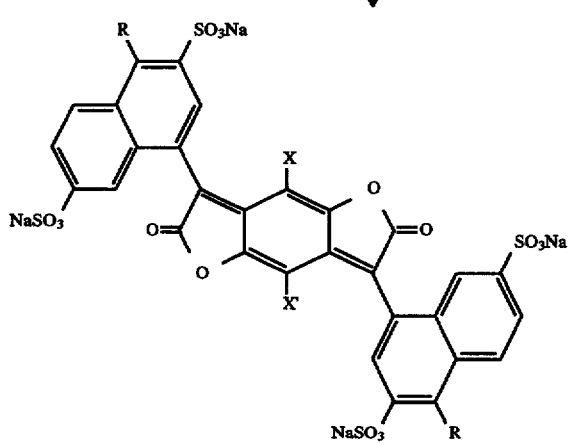

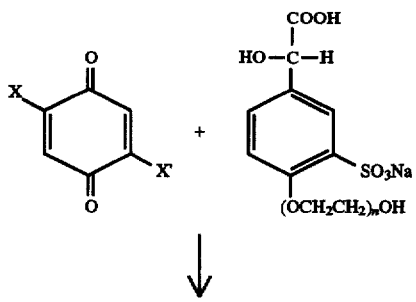

-continued

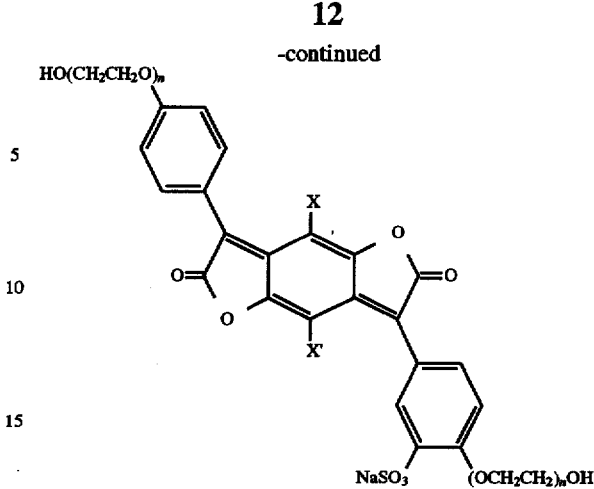

Starting or intermediate materials can be obtained or prepared by any desired or suitable method. For example, the sulfonated and ethoxylated staffing materials can be prepared from 4-hydroxymandelic acid (available from, for example, Aldrich Chemical Co., Milwaukee, Wisc.) or the naphthalene equivalent. One example of a suitable synthesis for the sulfonated material is as follows:

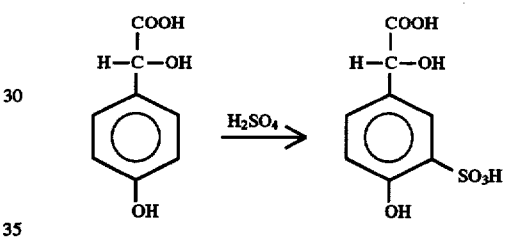

Direct sulfonation leads to attack on the ring adjacent to the phenolic hydroxy group. If desired, the acid groups can be converted to the corresponding salt (such as a sodium salt) by reaction with the desired hydroxide (such as, for example, sodium hydroxide). One example of a suitable synthesis for the polyethoxylated material is as follows:

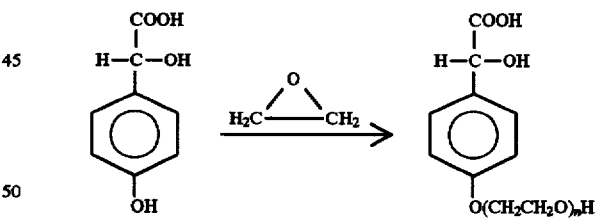

Under basic conditions, the acid group is in the —COO— salt form, and does not interfere with the ethoxylation. In addition, the rate of ethoxylation of the phenolic hydroxy group is from about 30 to about 40 times faster than the rate of ethoxylation of the secondary alcohol hydroxy group. Once the phenolic hydroxy group is ethoxylated, rapid chain growth occurs at this site. The ethoxylation generally is carried out at elevated temperatures (typically from about 120° to about 220° C.), optionally under pressure and in the presence of a catalyst. The reaction time is shortened by working under pressure, with preferred pressures being from about 1.5 to about 5.0 atmospheres. Alkaline catalysts such as caustic soda powder, sodium methylate, metallic sodium, or solid caustic potash generally are used at concentrations of from about 0.1 to about 1.5 percent by weight of the starting materials. The reaction is initiated by heating to a certain temperature which is then maintained to ensure a satisfactory reaction velocity and product quality. The required quantity of ethylene oxide is added in portions to the reaction mixture. Because of the exothermic nature of the reaction, no further supply of heat is usually required at this stage, and cooling may be desirable.

The dyes of the present invention vary in color depending on the substituents thereon. For example, when the R, R', S, and S' groups are neutral or slightly electron withdrawing, the dye generally has a yellow color. When the R, R', S, and S' groups are slightly electron donating, such as —OH groups, the dye generally has a magenta color. When the R, R', S, and S' groups are strongly electron donating, such as amine groups, the dye generally has a cyan color.

In aqueous ink compositions, such as those suitable for use in ink jet printing, particularly thermal ink jet printing, the colorant is present in the ink in any amount effective to obtain the desired color and intensity. Typically, the colorant is present in the ink in an amount of from about 0.1 to about 15 percent by weight, preferably from about 0.5 to about 10 percent by weight, and more preferably from about 1 to about 5 percent by weight, although the amount can be outside these ranges.

Aqueous ink compositions, such as those suitable for use in ink jet printing, particularly thermal ink jet printing, generally also contain a humectant. The humectant typically is an organic material miscible with water. Examples of suitable humectants include ethylene glycol, propylene glycol, diethylene glycols, glycerine, dipropylene glycols, polyethylene glycols, polypropylene glycols, amides, urea, substituted ureas, ethers, carboxylic acids, esters, alcohols, organosulfides, organosulfoxides, sulfones (such as sulfolane), alcohol derivatives, carbitol, butyl carbitol, cellusolve, ether derivatives, amino alcohols, ketones, N-methylpyrrolidinone, 2-pyrrolidinone, cyclohexylpyrrolidone, hydroxyethers, amides, sulfoxides, lactones, and other water miscible materials, as well as mixtures thereof. The humectant can be present in the ink composition in any effective amount. Typically, the humectant is present in an amount of from about 3 to about 70 percent by weight, preferably from about 5 to about 50 percent by weight, and more preferably from about 10 to about 30 percent by weight, although the amount can be outside these ranges.

Other additives can also be present in the inks. For example, one or more surfactants or wetting agents can be added to the ink. These additives may be of the cationic, anionic, or nonionic types. Suitable surfactants and wetting agents include sodium lauryl sulfate, Tamol® SN, Tamol® LG, those of the Triton® series available from Rohm and Haas Company, those of the Marasperse® series, those of the Igepal® series available from GAF Company, those of the Tergitoi® series, and other commercially available surfactants. These surfactants and wetting agents are present in effective amounts, generally from 0 to about 15 percent by weight, and preferably from about 0.01 to about 8 percent by weight, although the amount can be outside of this range.

Polymeric additives can also be added to the inks to enhance the viscosity and the stability of the ink. Water soluble polymers such as Gum Arabic, polyacrylate salts, polymethacrylate salts, polyvinyl alcohols, hydroxy propylcellulose, hydroxyethylcellulose, polyvinylpyrrolidinone, polyvinylether, starch, polysaccharides, polyethylene oxide, block copolymers of polyethylene oxide and polypropylene oxide, polyvinylpyridine, polyethyleneimine, polyhydroxyethyl ethyleneimine, polyquaternary salts, and the like are typical polymeric additives. Polymeric additives can be present in the ink of the present invention in amounts of from 0 to about 10 percent by weight, and preferably from about 0.01 to about 5 percent by weight, although the amount can be outside this range.

One example of an additive to the inks is a polymeric additive consisting of two polyalkylene oxide chains bound to a central bisphenol-A-type moiety. This additive is of the formula

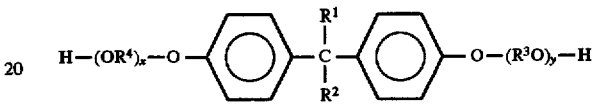

wherein $R^1$ and $R^2$ are independently selected from the group consisting of hydrogen, alkyl groups with from 1 to about 8 carbon atoms, such as methyl, ethyl, propyl, and the like, and alkoxy groups with from 1 to about 8 carbon atoms, such as methoxy, ethoxy, butoxy, and the like, $R^3$ and $R^4$ are independently selected from the group consisting of alkyl groups with from 1 to about 4 carbon atoms, and x and y are each independently a number of from about 100 to about 400, and preferably from about 100 to about 200. Generally, the molecular weight of the polyalkylene oxide polymer is from about 14,000 to about 22,000, and preferably from about 15,000 to about 20,000, although the molecular weight can be outside this range. Materials of this formula are commercially available; for example, Carbowax M20, a polyethylene oxide/bisphenol-A polymer of the above formula with a molecular weight of about 18,000, available from Union Carbide Corporation, Danbury, Conn., is a suitable polymeric additive for the inks of the present invention. In addition, compounds of the above formula can be prepared by the methods disclosed in *Polyethers*, N. G. Gaylord, John Wiley & Sons, New York (1963) and "Laboratory Synthesis of Polyethylene Glycol Derivatives," J. M. Harris, *J. Molecular Science—Rev. Macromol. Chem. Phys.*, C25(3), 325–373 (1985), the disclosures of each of which are totally incorporated herein by reference. The polyalkylene oxide additive is generally present in the ink in an amount of at least about 1 part per million. Typically, the polyalkylene oxide additive is present in amounts of up to 1 percent by weight of the ink, and preferably in amounts of up to 0.5 percent by weight of the ink; larger amounts of the additive may increase the viscosity of the ink beyond the desired level, but larger amounts can be used in applications wherein increased ink viscosity is not a problem. Inks containing these additives are disclosed in U.S. Pat. No. 5,207,825, the disclosure of which is totally incorporated herein by reference.

Other optional additives to the inks include biocides such as Dowicil 150, 200, and 75, benzoate salts, sorbate salts, and the like, present in an amount of from about 0.0001 to about 4 percent by weight, and preferably from about 0.01 to about 2.0 percent by weight, pH controlling agents such as acids or, bases, phosphate salts, carboxylates salts, sulfite salts, amine salts, and the like, present in an amount of from 0 to about 1 percent by weight and preferably from about 0.01 to about 1 percent by weight, or the like.

The ink compositions are generally of a viscosity suitable for use in thermal ink jet printing processes. Typically, the ink viscosity is no more than about 5 centipoise, and preferably is from about 1 to about 2.5 centipoise, although the viscosity can be outside this range.

Ink compositions suitable for ink jet printing can be prepared by any suitable process. Typically, the inks are prepared by simple mixing of the ingredients. One process entails mixing all of the ink ingredients together and filtering the mixture to obtain an ink. Inks can be prepared by preparing a conventional ink composition according to any desired process, such as by mixing the ingredients, heating if desired, and filtering, followed by adding any desired additional additives to the mixture and mixing at room temperature with moderate shaking until a homogeneous mixture is obtained, typically from about 5 to about 10 minutes. Alternatively, the optional ink additives can be mixed with the other ink ingredients during the ink preparation process, which takes place according to any desired procedure, such as by mixing all the ingredients, heating if desired, and filtering.

The present invention is also directed to a process which entails incorporating an ink composition of the present invention into an ink jet printing apparatus and causing droplets of the ink composition to be ejected in an imagewise pattern onto a substrate. In a particularly preferred embodiment, the printing apparatus employs a thermal ink jet process wherein the ink in the nozzles is selectively heated in an imagewise pattern, thereby causing droplets of the ink to be ejected in imagewise pattern. Any suitable substrate can be employed, including plain papers such as Xerox® 4024 papers, ruled notebook paper, bond paper, silica coated papers such as Sharp Company silica coated paper, JuJo paper, and the like, transparency materials, fabrics, textile products, plastics, polymeric films, inorganic substrates such as metals and wood, and the like. In a preferred embodiment, the process entails printing onto a porous or ink absorbent substrate, such as plain paper.

Specific embodiments of the invention will now be described in detail. These examples are intended to be illustrative, and the invention is not limited to the materials, conditions, or process parameters set forth in these embodiments. All parts and percentages are by weight unless otherwise indicated.

EXAMPLE I

A mixture of 2.2 parts of hydroquinone, 10.2 parts of α-hydroxy-3-sulfophenyl acetic acid, and 20 parts of 73% sulfuric acid is stirred at 120° C. for 5 minutes. The mixture is cooled and poured into water, and the colorless precipitated solid is filtered off, washed with water, then washed with diethylether, and dried.

A mixture of 1 part of this solid, 20 parts of acetic acid and 5 parts of 100 vol hydrogen peroxide solution is stirred at a boil under a reflux condenser. The mixture is diluted with water, and the precipitated orange solid is filtered off, washed with water and dried. Crystallization from a mixture of water and ethanol gives 3:7-di-3-sulfophenyl-2:6-dioxo-2:6-dihydrobenzo [1:2-b; 4:5-b$^1$] difuran.

EXAMPLE II

A mixture of 2.2 parts of hydroquinone, 10.2 parts of α-hydroxy-3-sulfophenyl acetic acid, 20 parts of acetic acid, and 1 part of sulfuric acid is stirred for 4 hours at a boil under a reflux condenser. The mixture is cooled to 30° C., 2 parts of 100 vol hydrogen peroxide solution are added, and the mixture is stirred at the boil for 1.5 hours. The mixture is then poured into 300 parts of ice and water, and the precipitated solid is filtered off. After extraction with boiling ethanol the residue is crystallized from a mixture of water and ethanol to give 3:7-di-3-sulfophenyl-2:6-dioxo-2:6-dihydrobenzo [1:2-b; 4:5-b$^1$] difuran.

EXAMPLE III

A mixture of 5.5 parts of hydroquinone and 23.2 parts of α-hydroxy-3-sulfophenyl acetic acid is stirred for 4 hours at 195°–200° C. The mixture is then cooled to 100° C. 100 parts of acetic acid and 10 parts of a 100 vol hydrogen peroxide solution are added, and the mixture is stirred for 1 hour at a boil. The mixture is then cooled, and the precipitated solid is filtered off, washed with acetic acid, then washed with methanol, and dried to give 3:7-di-3-sulfophenyl-2:6-dioxo-2:6-dihydrobenzo [1:2-b; 4:5-b$^1$] difuran.

EXAMPLE IV

A mixture of 4.2 parts of 1:4-benzoquinone, 27.4 parts of α-hydroxy-3-sulfophenyl acetic acid, and 30 parts of trichlorobenzene is stirred for 7 hours at 180° C. The mixture is then cooled to 20° C. and the precipitated dyestuff is filtered off, washed with toluene, then washed with a light petroleum fraction, and dried to give 3:7-di-3-sulfophenyl-2:6-dioxo-2:6-dihydrobenzo [1:2-b; 4:5-b$^1$] difuran.

EXAMPLE V

A mixture of 4.9 parts of chloranil (2:3:5:6-tetrachlorobenzoquinone), 18 parts of α-hydroxy-3-sulfophenyl acetic acid, and 25 parts of trichlorobenzene is stirred for 20 hours at 180° C. The mixture is then cooled to 20° C. and the precipitated solid is filtered off, washed with trichlorobenzene and then crystallized from a mixture of water and ethanol to yield a solid yellow dye.

EXAMPLE VI

A mixture of 5 parts of 2:3:5:6-tetrachlorohydroquinone, 6.7 parts of α-hydroxy-3-sulfophenyl acetic acid, and 50 parts of o-dichlorobenzene is stirred for 24 hours at a boil under a reflux condenser. The mixture is then cooled and the precipitated solid is filtered off, washed with trichlorobenzene and then crystallized from a mixture of water and ethanol to yield a solid yellow dye.

EXAMPLE VII

A mixture of 3.6 parts of 2:5-dichlorohydroquinone and 9.15 parts of α-hydroxy-3-sulfophenyl acetic acid is stirred for 2 hours at 210°–220° C. The mixture is then cooled to 120° C. 25 parts of isopropanol are added, the mixture is further cooled to 30° C., and water is then added until a solution of the product is obtained. The solution is filtered, the filtrate evaporated to dryness in vacuo, and the resulting solid is crystallized from a mixture of water and ethanol to yield orange crystals.

EXAMPLE VIII

A mixture of 2.45 parts of chloranil, 6 parts of 3-sulfophenylacetic acid, 0.5 part of zinc chloride, and 25 parts of trichlorobenzene is stirred for 1.75 hours at 190°–200° C. The mixture is then cooled to 20° C. The solid is filtered off, washed with a light petroleum ether and dried. The product is the same as that produced by the process of Example V.

EXAMPLE IX

A mixture of 4.25 parts of bromanil, 12 parts of 3-sulfophenylacetic acid, and 25 parts of trichlorobenzene is stirred for 1 hour at a boil. The mixture is cooled, and the precipitated solid is filtered off, washed with chlorobenzene, then washed with ethanol, and dried to yield 4:8-dibromo-3:7-di-3-sulfophenyl-2:6-dioxo-2:6-dihydrobenzo [1:2-b; 4:5-b¹] difuran, which is somewhat water soluble.

EXAMPLE X

A mixture of 4.24 parts of bromanil, 7.63 parts of p-methoxy-3-sulfophenyl acetic acid, and 25 parts of trichlorobenzene is stirred for 45 minutes at a boil. The mixture is then cooled. 25 parts of ethanol are added, and the precipitated solid is filtered off, washed with ethanol and dried to yield 4:8-dibromo-3:7-di(p-methoxy-3-sulfophenyl)-2:6-dioxo-2:6-dihydrobenzo[1:2-b; 4:5-b¹] difuran in the form of a red solid. The product dissolves in water to give a brighter red solution.

EXAMPLE XI

The process of Example X is repeated except that the 7.63 parts of p-methoxy-3-sulfophenyl acetic acid are replaced with equivalent amounts of the materials listed below. Reaction times vary from about 45 minutes to about 6 hours.

3,4-dimethoxy-5-sulfophenyl acetic acid 3-sulfo-4-tolylacetic acid 3-sulfo-4-(4'-methoxyphenyl)phenyl acetic acid 3-sulfo-4-iodophenyl acetic acid 3-sulfo-4-chlorophenyl acetic acid 3-nitro-5-sulfophenyl acetic acid 3-ethoxycarbonylphenyl-5-sulfophenyl acetic acid It is believed that similar results will be obtained. The dyes obtained vary in color depending on the substituents present; for example, those with strongly electron donating groups in the 2 or 4 positions of the phenyl groups generally have red or bluish colors.

EXAMPLE XII

A mixture of 4.24 parts of bromanil, 14.3 parts of ethyl 4-N,N-diethylamino-3-sulfophenyl acetate, and 10 parts of trichlorobenzene is stirred and heated at 185°–190° C. for 2 hours. After cooling the mixture, the solvent is removed by steam distillation and the residue is crystallized from toluene to yield 4,8-dibromo-3,7-di(p-N,N-diethylamino-3-sulfophenyl)-2,6-dioxo-2,6-dihydrobenzo [1:2-b; 4:5-b¹] difuran. When dissolved in water, a bright greenish turquoise solution is obtained.

EXAMPLE XIII

The processes of Examples I to XII are repeated except that the 3-sulfophenylacetic acid used therein is replaced with an equivalent amount of the corresponding disulfonated naphthylacetic acid. For example, in instances when an acid of the formula

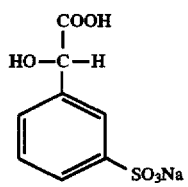

was employed, the corresponding disulfonated acid is of the formula

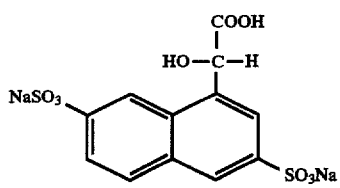

It is believed that similar results will be obtained, except that the aqueous solubility of the dye obtained is improved. Employing the disulfonated naphthylacetic acid instead of the monosulfonated phenylacetic acid increases the ratio of ring groups to solubilizing groups to 7:4, which is a much more favorable ratio than the 5:2 ratio for the monosulfonated phenylacetic acid generated dyes with respect to water solubility.

EXAMPLE XIV

In a 3 liter three-necked flask is placed a mixture of 170 grams (1 mole) of 4-hydroxymandelic acid (obtained from Aldrich Chemical Co., Milwaukee, Wisc.) and 175 grams (95 milliliters, 1.75 moles) of concentrated sulfuric acid, and the mixture is heated on a boiling water bath for three hours with constant mechanical stirring. At the end of this time the boiling water bath is replaced by an ice bath. When the reaction mixture has been cooled to room temperature it is made alkaline by the careful addition of a solution of 140 grams (3.5 moles) of sodium hydroxide in 350 milliliters of water. A solid salt forms and is removed by filtration. The resulting product is of the formula

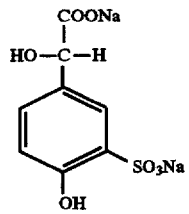

EXAMPLE XV

About 478 kilograms of dry 4-hydroxymandelic acid are introduced into an iron reactor vessel of 3 cubic meter capacity with a heating/cooling coil and a 500 rpm capacity stirrer reactor and heated to 150° C. Sodium hydroxide in an amount of about 1.5 percent by weight of the acid is added as a catalyst followed by removal of air from the vessel. Thereafter, about 1022 kilograms of ethylene oxide are fed successively to the reactor while stirring is maintained. The temperature increases because of the heat of the reaction, and temperature is maintained at from about 180° to about 210° C. The pressure in the reactor is maintained at from about 0.8 to about 1.2 atmospheres. The reaction is allowed to proceed for about 4 hours, followed by neutralization with hydrochloric acid to yield the product, believed to be of the formula

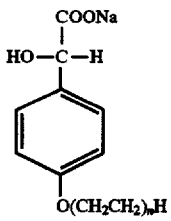

wherein n is an integer ranging from about 1 to about 20.

EXAMPLE XVI

The process of Example XVI is repeated except that the 4-hydroxymandelic acid is replaced with an equivalent amount of the product obtained in Example XV. The resulting product is believed to be of the formula

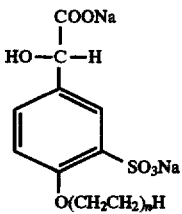

EXAMPLE XVII

The processes of Examples I to XIII are repeated except that the 3-sulfophenylacetic acid used therein is replaced with an equivalent amount of the reaction product of Example XIV. It is believed that similar results will be obtained.

EXAMPLE XVIII

The processes of Examples I to XIII are repeated except that the 3-sulfophenylacetic acid used therein is replaced with an equivalent amount of the reaction product of Example XV. It is believed that similar results will be obtained.

EXAMPLE XIX

The processes of Examples I to XIII are repeated except that the 3-sulfophenylacetic acid used therein is replaced with an equivalent amount of the reaction product of Example XVI. It is believed that similar results will be obtained.

Other embodiments and modifications of the present invention may occur to those skilled in the art subsequent to a review of the information presented herein, these embodiments and modifications, as well as equivalents thereof, are also included within the scope of this invention.

What is claimed is:

1. An ink jet printing process which comprises (1) incorporating into an ink jet printer an aqueous ink composition which comprises water, a humectant, and a colorant of the formula

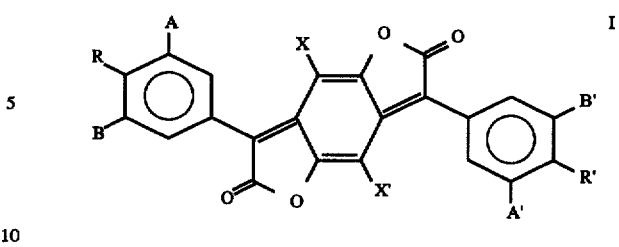

wherein (a) X and X' each, independently of one another, are hydrogen, alkyl, halogen, ester, or amide; (b) R and R' each, independently of one another, are hydrogen, hydroxy, alkoxy, aryloxy, ester, amine, amide, ether, thioether, or —(O(CH$_2$)$_y$)$_z$OH wherein y is an integer of from 1 to 3 and z is an integer of from 1 to about 50; (c) A, A', B, and B' each, independently of one another, are hydrogen, —COOH, —SO$_3$M, wherein M is a cation, or —NR"R"', wherein R" and R"' each, independently of one another, are hydrogen, alkyl, or aryl, wherein at least one of A, A', B, and B' is not hydrogen; or

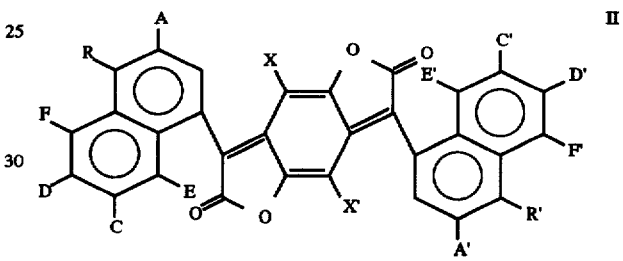

wherein (a) X and X' each, independently of one another, are hydrogen, alkyl, halogen, ester, or amide; (b) R and R' each, independently of one another, are hydrogen, hydroxy, alkoxy, aryloxy, ester, amine, amide, ether, thioether, or —(O(CH$_2$)$_y$)$_z$OH, wherein y is an integer of from 1 to 3 and z is an integer of from 1 to about 50; (c) A, A', C, C', D, D', E, E', F, and F' each, independently of one another, are hydrogen, —COOH, —SO$_3$M, wherein M is a cation, or —NR"R"', wherein R" and R"' each, independently of one another, are hydrogen, alkyl, or aryl, wherein at least one of A, A' C, C', D, D', E, E', F, and F' is not hydrogen; or

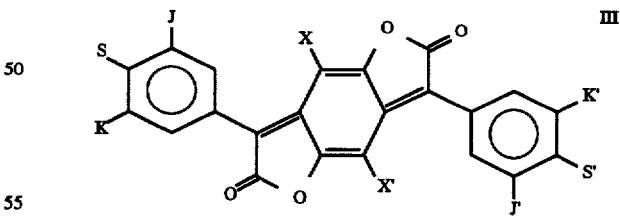

wherein (a) X and X' each, independently of one another, are hydrogen, alkyl, halogen, ester, or amide; (b) S and S' each, independently of one another, are hydrogen or —(O(CH$_2$)$_y$)$_z$OH, wherein y is an integer of from 1 to 3 and z is an integer of from 1 to about 50, wherein at least one of S and S' is not hydrogen; (c) J, J', K, and K' each, independently of one another, are hydrogen, —COOH, —SO$_3$M, wherein M is a cation, or —NR"R"', wherein R" and R"' each, independently of one another, are hydrogen, alkyl, or aryl; or

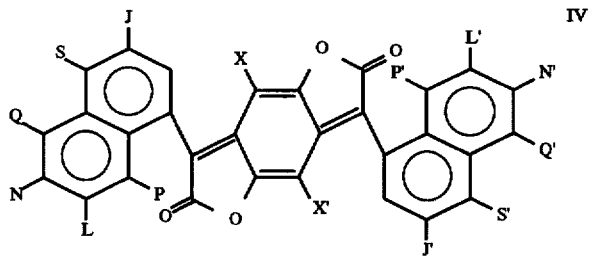

wherein (a) X and X' each, independently of one another, are hydrogen, alkyl, halogen, ester, or amide; (b) S and S' each, independently of one another, are hydrogen or —(O(CH$_2$)$_y$)$_z$OH, wherein y is an integer of from 1 to 3 and z is an integer of from 1 to about 50, wherein at least one of S and S' is not hydrogen; (c) J, J' L, L', N, N', P, P', Q, and Q' each, independently of one another, are hydrogen, —COOH, —SO$_3$M, wherein M is a cation, or —NR"R'", wherein R" and R'" each, independently of one another, are hydrogen, alkyl, or aryl; and (2) causing droplets of the ink composition to be ejected in an imagewise pattern onto a substrate.

2. A process according to claim 1 wherein the printing apparatus employs a thermal ink jet process wherein the ink in the nozzles is selectively heated in an imagewise pattern, thereby causing droplets of the ink to be ejected in imagewise pattern.

3. A process according to claim 1 wherein the colorant is present in the ink in an amount of from about 0.1 to about 15 percent by weight.

4. A process according to claim 1 wherein the colorant is present in the ink in an amount of from about 0.5 to about 10 percent by weight.

5. A process according to claim 1 wherein the colorant is present in the ink in an amount of from about 1 to about 5 percent by weight.

6. A process according to claim 1 wherein X and X' are each selected from the group consisting of (a) alkyl groups with from 1 to about 5 carbon atoms, (b) ester groups of the formula —C(O)OR, wherein R is an alkyl group with from 1 to about 5 carbon atoms or an aryl group with from about 6 to about 12 carbon atoms, and (c) amide groups of the formula —CONRR", wherein R and R' each, independently of the other, are alkyl groups with from 1 to about 5 carbon atoms or aryl groups with from 6 to about 12 carbon atoms.

7. A process according to claim 1 wherein R and R' each are selected from the group consisting of (a) alkoxy groups wherein the alkyl portion has from 1 to about 5 carbon atoms, (b) aryloxy groups with from about 6 to about 12 carbon atoms, (c) ester groups of the formula —C(O)OR, wherein R is an alkyl group with from 1 to about 5 carbon atoms or an aryl group with from about 6 to about 12 carbon atoms, (d) amine groups of the formula —NRR'R", wherein R, R', and R" each, independently of one another, are hydrogen atoms, alkyl groups with from 1 to about 5 carbon atoms, or aryl groups with from about 6 to about 12 carbon atoms, (e) amide groups of the formula —C(O)NRR', wherein R and R' each, independently of one another, are hydrogen atoms, alkyl groups with from 1 to about 5 carbon atoms, or aryl groups with from 6 to about 12 carbon atoms, (f) ether groups of the formula —OR, wherein R is an alkyl group with from 1 to about 5 carbon atoms or an aryl group with from about 6 to about 12 carbon atoms, (g) thioether groups of the formula —SR, wherein R is an alkyl group with from 1 to about 5 carbon atoms or an aryl group with from 6 to about 12 carbon atoms, and (h) polyalkoxy groups of the formula —(O(CH$_2$)$_y$)$_z$OH, wherein y is an integer of from 1 to 3 and z is an integer of from 1 to about 20.

8. A process according to claim 1 wherein S and S' each are selected from the group consisting of hydrogen atoms and polyalkoxy groups of the formula —(O(CH$_2$)$_y$)$_z$OH, wherein y is an integer of from 1 to 3 and z is an integer of from 1 to about 20.

9. A process according to claim 1 wherein the colorant is magenta.

10. A process according to claim 1 wherein the colorant is yellow.

11. A process according to claim 1 wherein the colorant is cyan.

12. Dye compositions of the formula

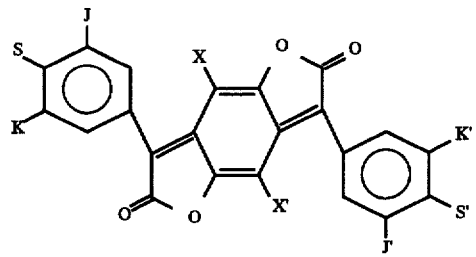

or

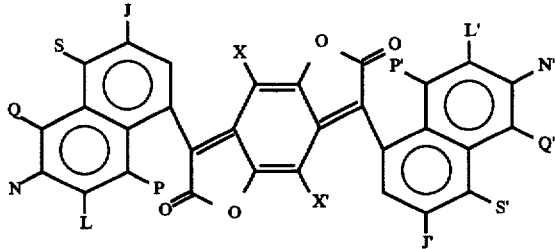

wherein (a) X and X' each, independently of one another, are hydrogen, alkyl, halogen, ester, or amide; (b) S and S' each, independently of one another, are hydrogen or —(O(CH$_2$)$_y$)$_z$OH, wherein y is an integer of from 1 to 3 and z is an integer of from 1 to about 50, wherein at least one of S and S' is not hydrogen; (c) J, J', K, K', L, L', N, N', P, P', Q, and Q' each, independently of one another, are hydrogen, —COOH, —SO$_3$M, wherein M is a cation, or —NR"R'", wherein R" and R'" each, independently of one another, are hydrogen, alkyl, or aryl.

13. A composition according to claim 12 wherein X and X' are each selected from the group consisting of (a) alkyl groups with from 1 to about 5 carbon atoms, (b) ester groups of the formula —C(O)OR, wherein R is an alkyl group with from 1 to about 5 carbon atoms or an aryl group with from about 6 to about 12 carbon atoms, and (c) amide groups of the formula —CONRR", wherein R and R' each, independently of the other, are alkyl groups with from 1 to about 5 carbon atoms or aryl groups with from 6 to about 12 carbon atoms.

14. A composition according to claim 12 wherein S and S' each are selected from the group consisting of hydrogen atoms and polyalkoxy groups of the formula —(O(CH$_2$)$_y$)$_z$OH, wherein y is an integer of from 1 to 3 and z is an integer of from 1 to about 20.

15. A composition according to claim 12 further containing a humectant and having a viscosity of from about 1 to about 5 centipoise.

16. A composition according to claim 12 further containing a humectant and having a viscosity of from about 1 to about 2.5 centipoise.

* * * * *